United States Patent
Sun et al.

(10) Patent No.: US 9,713,422 B2
(45) Date of Patent: Jul. 25, 2017

(54) FEMTOSECOND LASER SYSTEM FOR DETERMINING WHETHER THE CORNEA IS SUITABLE FOR LASIK SURGERY BY USING LASER-INDUCED PLASMA SPECTROSCOPIC ANALYSIS

(71) Applicant: Academy of Opto-Electronics, Chinese Academy of Sciences, Beijing (CN)

(72) Inventors: Hui Sun, Beijing (CN); Zhongwei Fan, Beijing (CN)

(73) Assignee: Academy of Opto-Electronics, Chinese Academy of Sciences, Beijing (CN)

( * ) Notice: Subject to any disclaimer, the term of this patent is extended or adjusted under 35 U.S.C. 154(b) by 0 days.

(21) Appl. No.: 15/089,746

(22) Filed: Apr. 4, 2016

(65) Prior Publication Data

US 2016/0338586 A1    Nov. 24, 2016

(30) Foreign Application Priority Data

May 21, 2015    (CN) .......................... 2015 1 0263383

(51) Int. Cl.
*A61B 3/10*    (2006.01)
*A61B 3/107*   (2006.01)
(Continued)

(52) U.S. Cl.
CPC ............ *A61B 3/107* (2013.01); *A61B 3/0025* (2013.01); *G02B 5/208* (2013.01); *G02B 5/3083* (2013.01);
(Continued)

(58) Field of Classification Search
CPC ....... A61B 3/102; A61B 3/107; A61B 5/0075; A61B 3/0008; A61B 18/20; A61B 5/0086
(Continued)

(56) References Cited

U.S. PATENT DOCUMENTS

2004/0183998 A1* 9/2004 Luce .................... A61B 3/1005
                                              351/212
2014/0368793 A1* 12/2014 Friedman ............. A61B 3/0025
                                              351/206

OTHER PUBLICATIONS

Sun Hui, et al., Optical Interactions with Tissue and Cells XXVII, Proc. of SPIE, vol. 9706, "Femtosecond laser subsurface scleral treatment in cadaver human sclera . . . ".
Sun Hui, et al., Journal of Biomedical Optics 17(7), Jul. 2012, "Finite element model of the temperature increase in excised porcine cadaver iris during direct . . . ".
Sun Hui, et al., Journal of Biomedical Optics 16(10), Oct. 2011, "Simulation of the temperature increase in human cadaver retina during direct illumination . . . ".
(Continued)

*Primary Examiner* — Hung Dang
(74) *Attorney, Agent, or Firm* — Buchanan Ingersoll & Rooney PC

(57) ABSTRACT

The present invention provides a laser system for detecting biomechanical properties of the cornea, which comprises a laser for emitting a pulsed laser beam, a beam transmission module, a collecting-filtering module and a spectroscopic analysis unit, the beam transmission module is used for transmitting the laser beam and focusing the laser beam onto the cornea, on the surface of which a laser-induced plasma signal is generated; the laser-induced plasma signals are collected and filtered by the collecting-filtering module; the spectroscopic analysis unit performs spectroscopic analysis on the laser-induced plasma signal to determine the biomechanical properties of the cornea. The present invention further provides a method for detecting the biomechanical properties of the cornea with the above laser system. The same laser system for LASIK surgery is utilized in the present invention to measure the biomechanical properties of the cornea timely and accurately, which improves work efficiency.

9 Claims, 2 Drawing Sheets

(51) Int. Cl.
    *A61B 3/00*     (2006.01)
    *G02B 27/14*     (2006.01)
    *G02B 5/20*     (2006.01)
    *G02B 5/30*     (2006.01)
    *G02B 27/09*     (2006.01)
    *G02B 27/30*     (2006.01)

(52) U.S. Cl.
    CPC ........ *G02B 27/0955* (2013.01); *G02B 27/141* (2013.01); *G02B 27/30* (2013.01)

(58) Field of Classification Search
    USPC ................ 351/221, 212, 206, 205, 200, 246
    See application file for complete search history.

(56) References Cited

OTHER PUBLICATIONS

Sun Hui, et al., Journal of Biomedical Optics 17(8), Aug. 2012, "Evaluation of human sclera after femtosecond laser ablation using two photon and confocal . . . ".

Sun Hui, et al., J Cataract Refract Surg 2011; 37:386-391, 2011, "Temperature increase in porcine cadaver iris during direct illumination by femtosecond laser pulses".

Sun Hui, et al., Lasers in Surgery and Medicine 39:654-658 (2007), "Femtosecond Laser Corneal Ablation Threshold: Dependence on Tissue Depth and Laser Pulse Width".

Sun Hui, et al., Optical Interactions with Tissue and Cells XXV; and Terahertz for Biomedical Applications, Proc. of SPIE vol. 8941, "Human Cadaver Retina Model . . . " (2014).

Sun Hui, et al., Optical Interactions with Tissue and Cells XXVI, , Proc. of SPIE vol. 9321, 93210A, "Porcine Cadaver Iris Model for Iris Heating during Corneal . . . " (2015).

* cited by examiner

FEMTOSECOND LASER SYSTEM FOR DETERMINING WHETHER THE CORNEA IS SUITABLE FOR LASIK SURGERY BY USING LASER-INDUCED PLASMA SPECTROSCOPIC ANALYSIS

TECHNICAL FIELD

The present invention relates to the field of laser, in particular to a laser system and a method for detecting biomechanical properties of the cornea.

BACKGROUND ART

Keratoconus is the most common cause for patients who are not suitable for laser in situ keratomileusis (LASIK) surgery, and currently, the keratoconus is one of the major clinical situations for the failure of LASIK surgery, where it must be taken into consideration whether a patient is prone to suffer keratoconus.

At present, the examination for keratoconus is to mainly measure the patient's corneal biomechanical parameters, as the corneal biomechanical parameters of patients suffering keratoconus are lower than normal levels.

Currently, an ocular response analyzer is the only clinical instrument for in vivo measurement of corneal biomechanical properties. Its measurement method is similar to that of a conventional non-contact tenonometer, where a patient is allowed to place his jaw on a holder of the instrument to fix the head, open his eyes as wide as possible with the to-be-tested eye gazing at a green flashing light in the instrument, a "measurement" button is pressed, then a instrument probe will automatically track and get close to the to-be-tested eye and blow out a surge of gas to flatten the cornea, and a range of parameters are measured. On the day of measurement with the ocular response analyzer, the to-be-tested eye must be kept away from any offensive operation and the use of eye drops, and the to-be-tested patient must be measured in the quiet and relaxed environment situations. Measurement is typically conducted for three times in each examination, but will be conducted for 5 times or even more when there are significant differences of measurement data, and the mean value is calculated.

Thus, it is noted that in measuring the corneal biomechanical properties with the current ocular response analyzer, there is a problem that measurement is affected by many factors, and particularly the patient state has a great influence on the measurement results, leading to a low preoperative examination efficiency for laser surgeries.

SUMMARY OF THE INVENTION

In view of the problem in the background art, the object of the present invention is to provide a laser system and a method for detecting biomechanical properties of the cornea, in order to accurately measure the biomechanical properties of the cornea in real time, to improve working efficiency.

The present invention adopts the following technical solution:

a laser system for detecting biomechanical properties of the cornea comprises a laser, a beam transmission module, a collecting-filtering module and a spectroscopic analysis unit, wherein the laser is used for emitting a pulsed laser beam;

the beam transmission module is used for transmitting the laser beam and focusing the laser beam onto the cornea, on the surface of which a laser-induced plasma signal is generated;

the collecting-filtering module collects and filters the laser-induced plasma signal, and transmits the laser-induced plasma signal to the spectroscopic analysis unit;

the spectroscopic analysis unit performs spectroscopic analysis on the laser-induced plasma signal, to determine the biomechanical properties of the cornea.

The present invention also provides a method for detecting biomechanical properties of the cornea with the laser system, comprising the steps of:

S1: starting the laser 1 to emit a laser beam;

S2: focusing the laser beam emitted in S1 onto the cornea, and generating the laser-induced plasma signal on the surface of the cornea;

S3: collecting and filtering the laser-induced plasma signal in S2;

S4: performing spectrographic analysis to the filtered laser-induced plasma signal in S3 to determine biomechanical properties of the cornea.

Compared with the prior art, in the laser system and the method for detecting the biomechanical properties of the cornea therewith of the present invention, a spectroscopic analysis unit is added to perform spectroscopic analysis on the laser induced plasma signal produced by the laser beams on the cornea, and determine the biomechanical properties of the cornea, which accurately and timely measures the biomechanical properties of the cornea with the same laser system.

Figure 1:
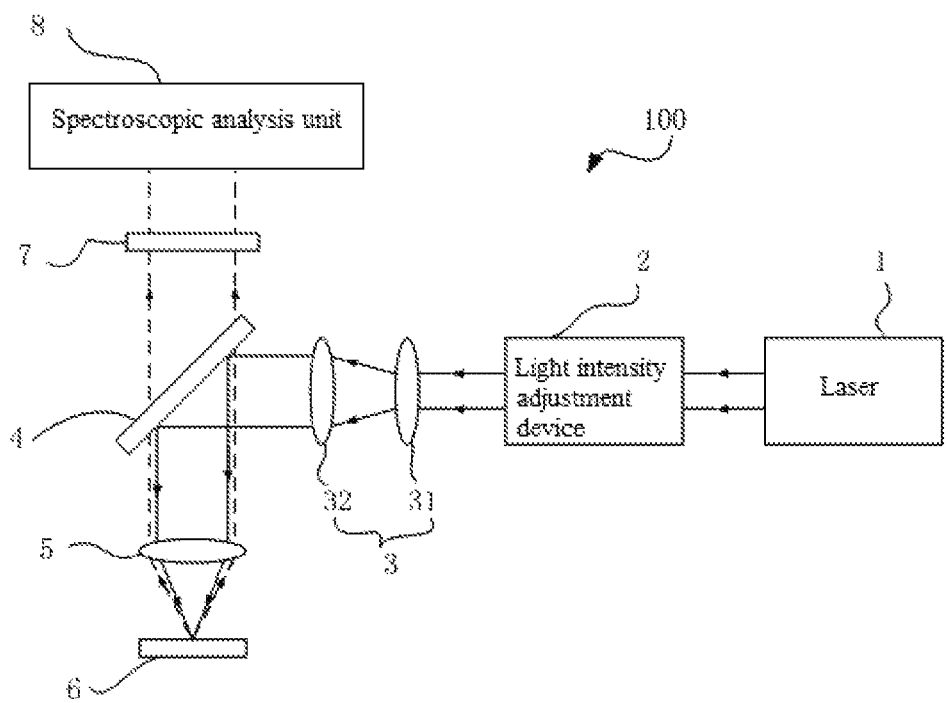
FIG. 1 is a schematic diagram of the laser system for detecting biomechanical properties of the cornea of the present invention.

Wherein, description of reference numerals is as follows:

| | |
|---|---|
| 100 | Laser system |
| 1 | Laser |
| 2 | Light intensity adjustment device |
| 3 | Laser beam expander |
| 31, 32 | Lenses |
| 4 | Dichroic mirror |
| 5 | Focusing lens |
| 6 | Cornea |
| 7 | Near-infrared filter |
| 8 | Spectroscopic analysis unit |

DETAILED DESCRIPTION OF THE INVENTION

To make the purpose, technical solution and advantages of the present invention more apparent, the present invention is further illustrated in conjunction with appended drawings and examples. It will be appreciated that specific examples are intended for purposes of illustration only, and should not be viewed as presenting any limitation on the invention.

Moreover, the technical features related to various embodiments of the invention described below can be combined with each other as long as they are not in a conflict. With reference to FIG. 1, the present invention provides a laser system 100 for detecting biomechanical properties of the cornea 6. The laser system 100 comprises a laser 1, a beam transmission module (not shown), a collecting-filtering module (not shown) and a spectroscopic analysis unit 8.

The focusing optical path of the laser system 1 is adopted for the optical path of the laser system 100. The laser 1 is used for emitting a pulsed laser beam; the beam transmission module is used for transmitting the laser beam from the laser 1 and focusing the laser beam onto the cornea 6, on the surface of which a laser-induced plasma signal is generated; the collecting-filtering module collects and filters the laser-induced plasma signal, and transmits the laser-induced plasma signal to the spectroscopic analysis unit 8; the spectroscopic analysis unit 8 performs spectroscopic analysis on the laser-induced plasma signal to determine the biomechanical properties of the cornea 6.

The laser system 1 may be any light source for producing laser spark, for example, can be, but is not limited to lasers such as a $CO_2$ laser, an Nd:YAG laser, a ruby laser, a titanium sapphire laser, a gallium arsenide laser, etc. In a preferred embodiment of the present invention, the laser 1 is a chirped pulse amplification all-solid-state femtosecond laser, wherein the femtosecond laser preferably produced by a femtosecond seed source has pulse-width of 180 femtoseconds, repetition rates of 90 MHz and average power of 90 mW, a stretcher stretches the seed source laser beam of 180 femtoseconds to 20 picoseconds, then the laser beam is injected into a regenerative amplifier through a magneto-optical isolator, and reciprocates in the regenerative amplifier for about 100 times, and the single pulse energy is incrementally enlarged to the maximum; the laser beam is emitted by the magneto-optical isolator to the regenerative amplifier, and then the laser pulse width is compressed from 20 picoseconds to 500 femtoseconds through a compressor. In a preferred embodiment of the present invention, the mode of the laser beam emitted by the laser 1 is a fundamental transverse mode, the beam quality factor is superior to 1.5, and the laser beam has good parallelism and small divergence angle.

The beam transmission module sequentially comprises a light intensity adjustment device 2, a laser beam expander 3, a dichroic mirror 4 and a focusing lens 5.

The light intensity adjustment device 2 is used for adjusting the light intensity of an incident laser from the laser 1, and guiding the incident laser to the laser beam expander 3. In the preferred embodiment, the light intensity adjustment device 2 is composed of a half-wave plate (not shown) and a polarizer (not shown), the half-wave plate rotates the vibration direction of the emergent laser so that not all the laser beam can pass through the polarizer, i.e., the laser beam is attenuated. Therefore, the laser transmittance of the light intensity adjustment device 2 can be changed by simply rotating the half-wave plate around the normal, thereby enabling precise attenuation control over the intensity of the incident laser.

The laser beam expander 3 is used for expanding and collimating the laser beam. In the preferred embodiment, the laser beam expander 3 comprises a lens 31 and a lens 32 with different focal lengths for expanding the diameter of the laser beam and decreasing the divergence angle of the laser beam; in the embodiment, the laser beam expander 3 is 5× beam expansion to simultaneously matching the laser beam expansion and divergence angle compression for better beam quality.

The dichroic mirror reflects the expanded and collimated laser beam, and the focusing lens 5 focuses the laser beam reflected by the dichroic mirror 4 onto the cornea 6, to generate laser-induced plasma signals on the surface of the cornea 6. The laser-induced plasma signals generated on the cornea 6 include laser-induced plasma signals generated by the cornea itself and laser-induced plasma signals generated by other substances in contact with the cornea, such as laser-induced plasma signals generated by lubricating liquid used for treating the cornea and the like.

The collecting-filtering module comprises a dichroic mirror 4 and a near-infrared filter 7, wherein the dichroic mirror 4 belongs to both the beam transmission module and the collecting-filter module.

The laser-induced plasma signals are transmitted sequentially through the focusing lens 5 and the dichroic mirror 4, and then the laser-induced plasma signals are mixed with some lasers refracted by the dichroic mirror 4.

The near-infrared filter 7 is used for filtering mixed light beam of the laser-induced plasma signals and lasers: the laser-induced plasma signals can be transmitted through the near-infrared filters 7, while the lasers are blocked by the near-infrared filter 7. The near-infrared filter 7 transmits the filtered laser-induced plasma signals to the spectroscopic analysis unit 8.

The spectroscopic analysis unit 8 receives and collects the above laser-induced plasma signals, and performs spectroscopic analysis on the laser-induced plasma signals. Since the spectrum of the laser-induced plasma signals generated by the cornea itself is different from that of the laser-induced plasma signals generated by other substances, the spectroscopic analysis unit 8 may clearly distinguish these two spectra, thereby removing the spectrum of the laser-induced plasma signals generated by other substances, and only performing spectroscopic analysis on the spectrum of the laser-induced plasma signals generated by the cornea itself, to clearly and accurately determine the biomechanical properties of the cornea of the patient.

Figure 2:
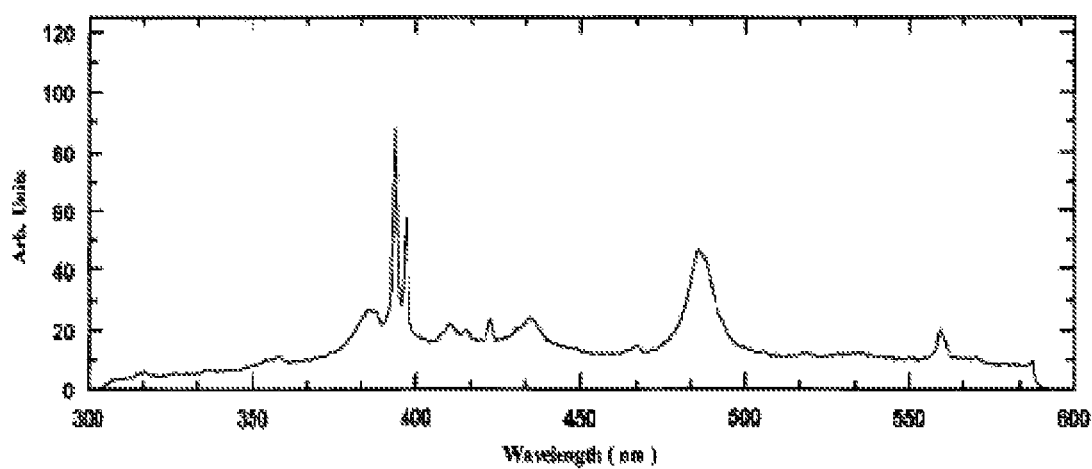
FIG. 2 is a spectrogram of the experimental verification performed by the laser system of the present invention used for detecting the biomechanical properties of the cornea.

Referring to FIG. 2, it is the spectrum of the laser-induced plasma signals generated by the cornea itself that is obtained through ablating the cornea 6 with the laser system 100 of the present invention and utilizing the spectroscopic analysis unit 8. FIG. 2 shows a spectrum from the cornea with normal biomechanical properties. If it is determined through the spectroscopic analysis unit 8 that the patient's cornea has normal biomechanical properties, the next cornea treating procedure is started.

Figure 3:
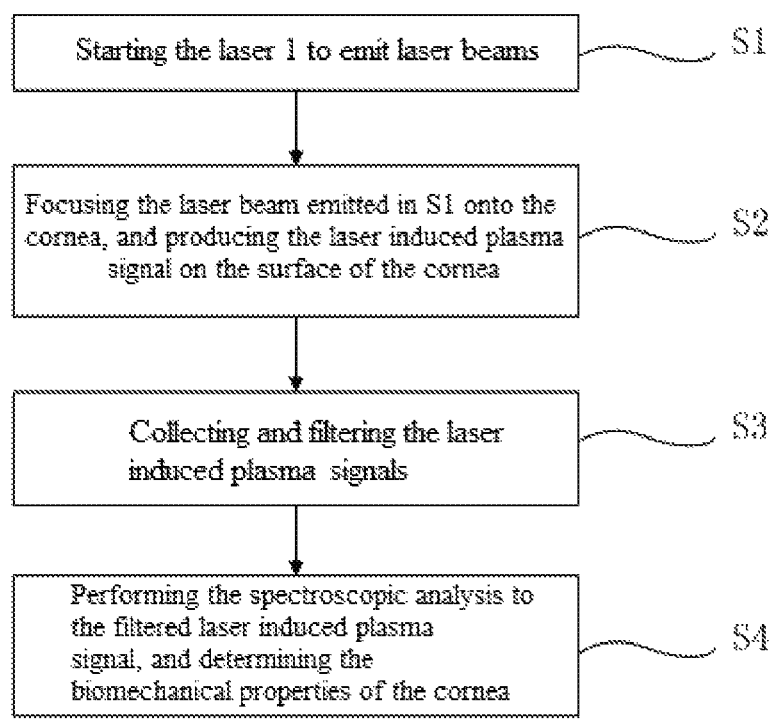
FIG. 3 is a method flowchart for detecting the biomechanical properties of the cornea with the laser system shown in FIG. 1.

Referring to FIG. 3, the present invention also provides a method for detecting biomechanical properties of the cornea with the laser system 100, comprising the steps of:

S1: starting the laser 1 to emit laser beam;

In a preferred embodiment of the present invention, the laser 1 is chirped pulse amplification all-solid-state femtosecond laser, wherein the femtosecond laser preferably produced by a femtosecond seed source has pulse-width of 180 femtoseconds, repetition rates of 90 MHz and average power of 90 mW, a stretcher stretches the seed source laser beam of 180 femtoseconds to 20 picoseconds, then the laser beam is injected into a regenerative amplifier through a magneto-optical isolator, and reciprocates in the regenerative amplifier for about 100 times, and the single pulse energy is incrementally enlarged to the maximum, then the laser beam is emitted by the magneto-optical isolator from the regenerative amplifier, and then the laser pulse width is compressed from 20 picoseconds to 500 femtoseconds through a compressor. In a preferred embodiment of the present invention, the mode of the laser beam emitted by the laser 1 is a fundamental transverse mode, the beam quality factor is superior to 1.5, and the laser beam has good parallelism and small divergence angle.

S2: focusing the laser beam emitted in S1 onto the cornea 6, and producing the laser-induced plasma signal on the surface of the cornea 6;

specifically, focusing the laser beam emitted in S1 onto the cornea 6 with the beam transmission module. The beam transmission module sequentially comprises a light intensity adjustment device 2, a laser beam expander 3, a dichroic mirror 4 and a focusing lens 5, wherein:

the light intensity adjustment device 2 is used for adjusting the light intensity of an incident laser from the laser 1, and guiding the incident laser to the laser beam expander 3. In the preferred embodiment, the light intensity adjustment device 2 is composed of a half-wave plate (not shown) and a polarizer (not shown), the half-wave plate rotates the vibration direction of the emergent laser so that not all the laser beam can pass through the polarizer, i.e., the laser beam is attenuated. Therefore, the laser transmittance of the light intensity adjustment device 2 can be changed by just rotating the half-wave plate around the normal, thereby realizing the precise attenuation control over the intensity of the incident laser.

The laser beam expander 3 is used for expanding and collimating the laser beams. In the preferred embodiment, the laser beam expander 3 comprises two lens 31 and lens 32 with different focal lengths for expanding the diameter of the laser beam and decreasing the divergence angle of the laser beam; in the embodiment, the laser beam expander 3 is 5-time beam expansion to simultaneously match the laser beam expansion and divergence angle compression for better beam quality.

The dichroic mirror 4 reflects the above expanded and collimated laser beams, and the focusing lens 5 focuses the laser beams reflected by the dichroic mirror 4 onto the cornea 6, to generate laser-induced plasma signals on the surface of the cornea 6. The laser-induced plasma signals generated on the cornea 6 include laser-induced plasma signals generated by the cornea itself and laser-induced plasma signals generated by other substances in contact with the cornea, such as the laser-induced plasma signals produced by a lubricating liquid and the like used for treating the cornea.

S3: collecting and filtering the laser-induced plasma signals;

specifically, collecting and filtering the laser-induced plasma signal produced in S2 with the collecting-filtering module. The collecting-filtering module comprises a dichroic mirror 4 and a near-infrared filter 7.

The laser-induced plasma signals are transmitted sequentially by the focusing lens 5 and the dichroic mirror 4, and at this time the laser-induced plasma signals are mixed with a part of lasers refracted by the dichroic mirror 4.

The near-infrared filter 7 is used for filtering the mixed light beams of the laser-induced plasma signals and the lasers, the laser-induced plasma signals can be transmitted through the near-infrared filters 7, while the lasers are blocked by the near-infrared filter 7.

S4: performing spectrographic analysis to the filtered laser-induced plasma signals in S3 to determine the biomechanical properties of the cornea 6.

Specifically, since the spectrum of the laser-induced plasma signals generated by the cornea itself is different from that of the laser-induced plasma signals generated by other substances, the spectroscopic analysis unit 8 may clearly distinguish these two spectra, thereby removing the spectrum of the laser-induced plasma signals generated by other substances, and only performing spectroscopic analysis on the spectrum of the laser-induced plasma signals generated by the cornea itself, to clearly and accurately determine the biomechanical properties of the cornea of the patient.

In the laser system 100 of the present invention and the method for detecting the biomechanical properties of the cornea with the laser system 100, the spectroscopic analysis unit 8 is added to perform spectroscopic analysis to laser induced plasma signal produced by the laser beam on the cornea 6, and determine the biomechanical properties of the cornea 6, so that the laser system 100 is used for accurately measuring the biomechanical properties of the cornea in real time, thus increasing the working efficiency.

The above description is just the preferred embodiments of the present invention, and is not intended to limit the scope of the protection, it is intended that the present invention covers any modifications, equivalents and improvements made within the spirit and principle of the present invention.

The invention claimed is:

1. A laser system for detecting the biomechanical properties of the cornea, wherein the laser system comprises a laser, a beam transmission module, a collecting-filtering module and a spectroscopic analysis unit, wherein the laser is used for emitting a pulsed laser beam;

the beam transmission module is used for transmitting and focusing the laser beam onto the cornea to generate a laser-induced plasma signal on the surface the cornea;

the collecting-filtering module is used for collecting and filtering the laser-induced plasma signal, and transmitting the laser-induced plasma signal to the spectroscopic analysis unit;

the spectroscopic analysis unit is used for performing spectroscopic analysis on the laser-induced plasma signal to determine the biomechanical properties of the cornea.

2. The laser system according to claim 1, wherein the beam transmission module sequentially comprises a light intensity adjustment device, a laser beam expander, a dichroic mirror and a focusing lens.

3. The laser system according to claim 2, wherein the light intensity adjustment device is formed by combining a half-wave plate and a polarizer.

4. The laser system according to claim 2, wherein the laser beam expander comprises two lenses of different focal lengths, which constitute a 5-time laser beam expansion and collimation system.

5. The laser system according to claim 1, wherein the collecting-filtering module comprises a dichroic mirror and a near-infrared filter.

6. The laser system according to claim 1, wherein the laser is a chirped pulse amplification all-solid-state femtosecond laser.

7. A method for detecting biomechanical properties of the cornea with the above-described laser system of claim 1, comprising the steps of:

S1: starting the laser to emit a laser beam;

S2: focusing the laser beam emitted in S1 onto the cornea, and generating the laser-induced plasma signal on the surface of the cornea;

S3: collecting and filtering the laser-induced plasma signal in S2;

S4: performing spectrographic analysis to the filtered laser-induced plasma signals in S3 to determine the biomechanical properties of the corneal.

8. The method for detecting the biomechanical properties of the cornea according to claim 7, wherein in step S2, the beam transmission module is utilized to transmit the laser beam and focus to the cornea, the beam transmission module sequentially comprises a light intensity adjustment device, a laser beam expander, a dichroic mirror and a focusing lens.

9. The method for detecting biomechanical properties of the cornea according to claim 8, wherein in step S3, the collecting-filtering module is utilized to collect and filter the laser-induced plasma signal, and the collecting-filtering module comprises a dichroic mirror and a near-infrared filter.

* * * * *